US012551356B2

(12) United States Patent
Barnes et al.

(10) Patent No.: US 12,551,356 B2
(45) Date of Patent: Feb. 17, 2026

(54) UNIVERSAL LATERAL PIVOTING HANDLE

(71) Applicant: Stryker Corporation, Portage, MI (US)

(72) Inventors: Liam Patrick Barnes, Ashburn, VA (US); Alexander Horia Artaki, Washington, DC (US); Pauline Patricia Hutton, Gainesville, VA (US)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 18/795,783

(22) Filed: Aug. 6, 2024

(65) Prior Publication Data

US 2025/0049583 A1 Feb. 13, 2025

Related U.S. Application Data

(60) Provisional application No. 63/531,390, filed on Aug. 8, 2023.

(51) Int. Cl.
*A61F 2/46* (2006.01)
*A61F 2/44* (2006.01)

(52) U.S. Cl.
CPC .......... *A61F 2/4611* (2013.01); *A61F 2/4455* (2013.01); *A61F 2002/4628* (2013.01)

(58) Field of Classification Search
CPC ......... A61F 2/46; A61F 2/4611; A61F 2/4455
See application file for complete search history.

(56) References Cited

U.S. PATENT DOCUMENTS 4,716,894 A 1/1988 Lazzeri et al.
5,284,483 A 2/1994 Johnson et al.
5,584,837 A 12/1996 Petersen
5,713,906 A 2/1998 Grothues-Spork et al.
6,238,435 B1 5/2001 Meulink et al.
6,524,238 B2 2/2003 Velikaris et al.
6,676,664 B1 1/2004 Al-Assir
7,008,430 B2 3/2006 Dong et al.
7,186,257 B2 3/2007 Kim
7,488,327 B2 2/2009 Rathbun et al.
7,549,998 B2 6/2009 Braun
(Continued)

FOREIGN PATENT DOCUMENTS

CA 2446934 A1 11/2002
CA 2477821 C 10/2012
(Continued)

OTHER PUBLICATIONS

Extended European Search Report including Search Opinion from EP Appl. No. 24193328.2, dated Jan. 2, 2025, pp. 1-11.

*Primary Examiner* — Si Ming Ku
(74) *Attorney, Agent, or Firm* — Lerner David LLP

(57) ABSTRACT

A surgical instrument to implant spinal implants including a shaft, a sleeve, and a handle assembly. The shaft defining a longitudinal axis and having a slotted portion with first slots and second slots. The sleeve rotatably disposed around the slotted portion. The handle assembly pivotably attached to the sleeve by a pivot pin, the handle assembly having a positioning tip sized to be received in the first and second slots of the slotted portion. The handle assembly can pivot about the pivot pin between a first position and a second position. In the first position, the positioning tip engages one of the first slots, while in the second position, the positioning tip engages one of the second slots.

20 Claims, 14 Drawing Sheets

(56) References Cited

U.S. PATENT DOCUMENTS 7,780,669 B2 8/2010 Lechot et al.
7,799,086 B2 9/2010 Justin et al.
8,062,375 B2 11/2011 Glerum et al.
8,303,662 B2 11/2012 Landry et al.
8,518,120 B2 8/2013 Glerum et al.
8,556,979 B2 10/2013 Glerum et al.
8,679,183 B2 3/2014 Glerum et al.
8,685,031 B2 4/2014 Kleiner et al.
8,685,098 B2 4/2014 Glerum et al.
8,709,086 B2 4/2014 Glerum
8,709,088 B2 4/2014 Kleiner et al.
8,771,282 B2 7/2014 Blain et al.
8,888,853 B2 11/2014 Glerum et al.
8,888,854 B2 11/2014 Glerum et al.
8,906,028 B2 12/2014 Kleiner et al.
8,926,704 B2 1/2015 Glerum et al.
9,039,771 B2 5/2015 Glerum et al.
9,060,877 B2 6/2015 Kleiner
9,078,672 B1 7/2015 Rosse
9,095,385 B2 8/2015 Wallenstein et al.
9,119,730 B2 9/2015 Glerum et al.
9,155,546 B2 10/2015 McCarthy et al.
9,155,628 B2 10/2015 Glerum et al.
9,173,694 B2 11/2015 Kleiner
9,186,193 B2 11/2015 Kleiner et al.
9,204,974 B2 12/2015 Glerum et al.
9,211,196 B2 12/2015 Glerum et al.
9,216,095 B2 12/2015 Glerum et al.
9,226,836 B2 1/2016 Glerum
9,358,126 B2 6/2016 Glerum et al.
9,358,128 B2 6/2016 Glerum et al.
9,421,020 B2 8/2016 Blain et al.
9,452,063 B2 9/2016 Glerum et al.
9,456,903 B2 10/2016 Glerum et al.
9,492,287 B2 11/2016 Glerum et al.
9,510,954 B2 12/2016 Glerum et al.
9,597,200 B2 3/2017 Glerum et al.
9,629,729 B2 4/2017 Grimberg, Jr. et al.
9,655,747 B2 5/2017 Glerum et al.
9,848,997 B2 12/2017 Glerum et al.
9,936,960 B2 4/2018 Weekes
9,949,841 B2 4/2018 Glerum et al.
9,956,087 B2 5/2018 Seifert et al.
9,962,271 B2 5/2018 Glerum
9,987,144 B2 6/2018 Seifert et al.
10,016,282 B2 7/2018 Seifert et al.
10,052,213 B2 8/2018 Glerum et al.
10,070,971 B2 9/2018 Palmatier et al.
10,098,758 B2 10/2018 Matthews et al.
10,137,006 B2 11/2018 Dewey et al.
10,154,912 B2 12/2018 Glerum
10,195,053 B2 2/2019 Kleiner et al.
10,219,913 B2 3/2019 Matthews et al.
10,226,359 B2 3/2019 Glerum et al.
10,245,159 B1 4/2019 Kleiner et al.
10,299,934 B2 5/2019 Seifert et al.
10,327,787 B2 6/2019 Brotman
10,327,917 B2 6/2019 Glerum et al.
10,350,081 B2 7/2019 Seifert et al.
10,350,085 B2 7/2019 Glerum et al.
10,376,377 B2 8/2019 Seifert et al.
10,610,376 B2 4/2020 Kuyler et al.
10,617,533 B2 4/2020 Glerum et al.
10,631,884 B2 4/2020 Thibodeau et al.
10,709,571 B2 7/2020 Iott et al.
10,744,002 B2 8/2020 Glerum et al.
10,799,368 B2 10/2020 Glerum et al.
10,806,596 B2 10/2020 Iott et al.
10,881,530 B2 * 1/2021 Donaldson ............ A61F 2/4611
10,959,856 B2 3/2021 Seifert et al.
10,973,656 B2 4/2021 Kleiner et al.
11,026,800 B2 6/2021 Seifert et al.
11,045,326 B2 6/2021 Seifert et al.
11,103,366 B2 8/2021 Glerum et al.
11,109,980 B2 9/2021 Seifert et al.
11,123,199 B2 9/2021 Seifert et al.
11,191,649 B2 12/2021 Matthews et al.
11,234,836 B2 2/2022 Glerum et al.
11,285,014 B1 3/2022 Josse et al.
11,291,554 B1 4/2022 Prevost et al.
11,331,126 B2 5/2022 Cha
11,337,826 B2 5/2022 Seifert et al.
11,344,430 B2 5/2022 Glerum et al.
11,364,130 B2 6/2022 Cowan et al.
11,376,134 B1 7/2022 Dewey et al.
11,395,743 B1 7/2022 Hynes et al.
11,399,958 B2 8/2022 Glerum et al.
11,471,145 B2 10/2022 Pacheco-Serrant et al.
11,517,363 B2 12/2022 Nayet et al.
11,517,443 B2 12/2022 Dewey et al.
11,564,724 B2 1/2023 Josse et al.
11,564,807 B2 1/2023 Iott et al.
11,571,315 B2 2/2023 Glerum
11,612,501 B2 3/2023 Pendleton et al.
11,617,658 B2 4/2023 Josse et al.
11,628,023 B2 4/2023 Troxell et al.
11,638,653 B2 5/2023 Nayet et al.
11,660,208 B2 5/2023 Kleiner et al.
11,666,455 B2 6/2023 Kleiner
11,666,457 B2 6/2023 Glerum et al.
11,690,733 B2 7/2023 Matthews et al.
11,723,780 B2 8/2023 Seifert et al.
2007/0233150 A1 10/2007 Blain et al.
2014/0142642 A1 * 5/2014 Wallenstein .......... A61F 2/4611 606/86 A
2016/0143649 A1 * 5/2016 Weekes .............. A61B 17/1622 606/80
2017/0216045 A1 8/2017 Dewey et al.
2018/0360621 A1 12/2018 Moon
2021/0030555 A1 2/2021 Weiman et al.
2022/0000633 A1 1/2022 Seifert et al.
2022/0039844 A1 2/2022 Cha
2022/0133495 A1 5/2022 Glerum et al.
2022/0133497 A1 5/2022 Dewey et al.
2022/0133499 A1 5/2022 Josse et al.
2022/0211520 A1 7/2022 Himmelberger et al.
2022/0226125 A1 7/2022 Seifert et al.
2022/0265437 A1 8/2022 Glerum et al.
2022/0304822 A1 9/2022 Glerum et al.
2022/0387184 A1 12/2022 Josse et al.
2023/0051745 A1 2/2023 Pacheco-Serrant et al.
2023/0172729 A1 6/2023 Josse et al.
2023/0181335 A1 6/2023 Josse et al.
2023/0255791 A1 8/2023 Kleiner

FOREIGN PATENT DOCUMENTS

CN 111419488 B 10/2022
DE 29607026 U1 7/1996
DE 60002017 T2 3/2004
EP 1389983 B1 8/2006
EP 2735287 B1 1/2020
EP 2830542 B1 10/2021
EP 3362000 B1 3/2023
FR 2977474 A1 1/2013
GB 2299758 B 7/1998
JP 4234443 B2 3/2009
KR 102240954 B1 4/2021
WO 2020185032 A2 9/2020

* cited by examiner

UNIVERSAL LATERAL PIVOTING HANDLE

CROSS-REFERENCE TO RELATED APPLICATIONS

The present application claims priority to U.S. Provisional Application No. 63/531,390, filed Aug. 8, 2023, the contents of which are incorporated herein by reference.

BACKGROUND

The present application relates to surgical instruments used during the insertion of spinal implants and methods of using such instruments. More particularly, the embodiments of the invention relate to modular instruments including a handle that can be oriented to various positions and angles suited for various interbody fusion procedures requiring insertion of intervertebral implants.

Intervertebral implants are commonly used in spinal surgery in which an implant (e.g., a spacer or cage) is placed in the disc space between two vertebrae to be fused together. One such type of application is an interbody fusion procedure. At least a portion of the disc is typically removed before the implant is positioned in the intervertebral space. The implant may be supplemented with bone graft material to promote fusion of the vertebrae. These procedures may also be performed in conjunction with other types of fixation, such as pedicle screw fixation, to provide additional stability, particularly while the vertebrae fuse together.

Interbody fusion procedures can be distinguished by the type of implant used, by their location along the spine (cervical, thoracic, or lumbar, for example), and by the surgical approach to the intervertebral space. Different surgical approaches may require the use of certain surgical instruments and implants which are designed or suited for the particular approach (for instance, anterior, posterior, and lateral approaches). Anterior to psoas approach (ATP) and direct lateral interbody fusion (DLIF) are examples of interbody fusion techniques performed along a lateral aspect. ATP techniques typically include positioning an intervertebral implant into the intervertebral space from a direction diagonal to the medial-lateral direction (i.e., an angled approach). On the other hand, DLIF techniques typically include positioning an intervertebral implant into the intervertebral space from a direction directly along the medial-lateral direction (i.e., a non-angled approach).

When it is desired to insert an implant to a final position that is angled with respect to the axis of insertion, particularly in an ATP procedure, specialized instruments are often useful in allowing final placement of the implant while maintaining a small surgical site. For example, angled instruments can permit access to more of the intervertebral disc space than a straight instrument may allow.

Further improvement is desired in the field of spinal implant instrumentation for devices that have increased functionality and durability for multiple uses.

BRIEF SUMMARY

Some aspects herein relate to an implant insertion instrument capable of modulating between straight and angled configurations, the instrument having a handle assembly including a handle extending away from the instrument. The handle assembly may be configured to allow the handle to rotate around the body of the instrument to discrete positions and to pivot between a forward and backward positions along the longitudinal axis of the instrument. In the forward position, the handle may be perpendicular to the longitudinal axis of the body of the instrument, while in the backward position, the handle may be diagonal to the longitudinal axis of the instrument. The handle assembly may also include a casing rotatably disposed around the central body of the handle assembly and having a receptacle extending therefrom, the receptacle configured to receive and attach to an end portion of the handle. The casing may have an interior region wider than the end portion of the handle such that the handle can shift between multiple positions therein.

The handle may be capable of actuating between an engaged state and a disengaged state without being disconnected from the handle assembly. The engaged state may be when a portion of the handle is inserted into a central body of the handle assembly or the instrument thereby creating a connection. The disengaged state may be when this connection is broken between the handle and the central body of the handle assembly or the instrument by temporarily retracting an insertion component of the handle away from the instrument, while the handle remains attached to the casing. The insertion component of the handle may be connected to an external collar that can be used to withdraw the insertion component and place the handle in the disengaged state. When in the disengaged state, the handle may be configured to rotate around and pivot along the longitudinal axis of the instrument while the handle is still connected to the casing. This allows the handle of the instrument to be oriented at different angles and extend in different directions from the instrument. In this manner, the location and angle of the handle can be adjusted to best fit various approaches for implant insertion.

In another aspect, a surgical instrument for implanting spinal implants may include a shaft, a sleeve, and a handle assembly. The shaft, defining a longitudinal axis, may have a slotted portion with first slots and second slots. The sleeve may be rotatably disposed around the slotted portion. The handle assembly may be pivotably attached to the sleeve by a pivot pin and may have a positioning tip that may be sized to be received in the first and second slots. The handle assembly may pivot about the pivot pin between a first position and a second position. In the first position, the positioning tip may engage one of the first slots. In the second position, the positioning tip may engage one of the second slots. In such arrangements, the surgical instrument may further include an actuator that may be disposed adjacent to the sleeve portion for engaging and disengaging the positioning tip with one of the first and second slots. In such arrangements, the actuator may be spring biased to engage the positioning tip with one of the first and second slots.

In other arrangements, each of the plurality of first slots are aligned with the plurality of second slots. The plurality of first and second slots may be disposed in the slotted section of the body portion. The slotted portion may include a non-angled portion and an angled portion. The first slots may be disposed radially around the non-angled portion, and the second slots may be disposed radially around the angled portion. The sleeve may include inner surfaces complementary to the non-angled and angled portions.

In accordance with another aspect, a handle assembly of an implant inserter may be adjusted by a process. In the process, a tip of a handle may be disengaged from one of a plurality of first slots in a shaft of the inserter. Next, the handle may be pivoted from a first position to a second position. Subsequently, the handle may be rotated about the shaft. Finally, the tip of the handle may engage with one of a plurality of second slots in the shaft. In such arrangements, the tip may be retracted and the handled pivoted back to the first position from the second position. The first position may be orthogonal to the longitudinal axis of the shaft and the second position is diagonal to the longitudinal axis of the shaft.

In other arrangements, in the process, the handle may be rotated about the shaft before engaging the tip of the handle. The tip of the handle may be retracted by retracting a collar disposed around an exterior of the handle and connected to an internal portion of the tip of the handle. After retracting the tip of the handle, rotating the handle by any one of 45°, 90°, 135°, 180°, 225°, 270°, 315°, or 360° around a body portion of the shaft. In such arrangements, the tip may be inserted into any one of a plurality of slots radially disposed around the body portion.

In some other arrangements, in the process, an apparatus may be disposed in a hollow annulus of the shaft. The disengaging of the tip of the handle may include removing the tip from a one of the plurality of first slots by pulling an actuator away from the shaft of the inserter. Retracting the actuator may include compressing a spring disposed within the handle. Engaging the tip may include the tip being inserted into one of the plurality of second slots in the shaft of the inserter by releasing the actuator such that the spring advances the tip toward the shaft of the inserter as the spring expands. Pivoting the handle may include holding the actuator such that the tip remains in a disengaged position.

In accordance with another aspect, a surgical instrument for inserting implants may include a body portion, a handle assembly, a sleeve portion. The body portion, defining a longitudinal axis, may have a first slot and a second slot. The handle assembly may have a handle or handgrip, a positioning tip, and a pivot pin. The sleeve portion may be disposed around the body portion and may have an extension portion that extends away from the body portion. The pivot pin may be rotatably engaged with or attached to the extension portion of the sleeve portion such that the handle may pivot between a first portion and a second position. The handle (i.e., handgrip) may be orthogonal to the longitudinal axis of the body portion in the first position and may be diagonal to the longitudinal axis of the body portion in the second position. The positioning tip of the handle may be coaxially aligned with the first slot in a first segment of the body portion when the handle is in the first position. The positioning tip of the handle may be coaxially aligned with the second slot in a second segment of the body portion when the handle is in the second position. In such arrangements, the body portion may include a plurality of first slots and a plurality of second slots. Both the plurality of first and second slots may be radially disposed around the body portion. The plurality of second slots may be oriented diagonal to the longitudinal axis.

In other arrangements, the body portion may include a distal section, an intermediate section, and a proximal section. The intermediate section may have the first segment and second segment therein. The distal section may have a larger diameter than the intermediate section. The second segment of the body portion may define a diameter that increases in the distal direction. The sleeve portion may be rotatably disposed around the intermediate section of the body portion. The handle may include an elongated slot arranged such that the pivot pin extends therethrough. The body portion may define a hollow annulus extending therethrough. The handle may be threadably attached to a connector component that is configured to connect the handle and the positioning tip, and the handle may extend away from the body portion. The handle assembly may be attached to a proximal end of a barrel portion of the surgical instrument.

In yet other arrangements, the extension portion of the sleeve portion may define a hollow interior configured to receive an end portion of the handle. The hollow inter of the extension portion may have an hourglass-like shape to allow the end portion of the handle to pivot between the first and second positions. The sleeve portion and handle may rotate around the body portion in unison. The handle may rotate around the body portion while oriented in the first position or second position. The end portion of the handle may include the positioning tip and the connector component. The connector component may have a hollow chamber configured to receive a spring and at least a portion of the positioning tip. The spring may be disposed between the positioning tip and the connector component within the hollow chamber. The handle may include a collar (i.e., an actuator) that may be slidably disposed around the hollow chamber and configured for engaging and disengaging the positioning tip with either one of the first or second slots. The connector component may include a backstop portion disposed adjacent to the hollow chamber. The backstop portion may extend radially out from the connector component and configured to restrict movement of the collar.

In yet in other arrangements, a cap may be threadably disposed on the proximal section of the body portion such that the cap is adjacent to the sleeve portion. The cap may be configured to prevent the sleeve from moving along the longitudinal axis of the body portion in the proximal direction. In some other arrangements, the first and second slots may have an oval shape. In such arrangements, the positioning tip may have an insertion portion that has an oval shape that conforms to the first and second slots. The insertion portion may have a smaller thickness than the remainder of the positioning tip. The insertion portion of the positioning tip may be the only feature of the handle that contacts the body portion. In some other arrangements, the sleeve portion covers the plurality of the first and second slots such that at least one of each of the plurality of first and second slots are aligned with a hollow interior of the extension portion of the sleeve at any given time or position.

In another arrangement, a surgical instrument for implanting spinal implants may include a shaft, a sleeve, and a handle assembly. The shaft, defining a longitudinal axis, may have a slotted portion that defines a first set of slots and a second set of slots. The sleeve may be rotatably disposed around the slotted portion. The handle assembly may be pivotably attached to the sleeve and may have a positioning tip that may be sized to be received by each of the first and the second set of slots. The handle assembly may pivot about a pivot point between a first position and a second position. In the first position, the positioning tip may be oriented to engage a slot of the first slots. In the second position, the positioning tip may be oriented to engage a slot of the second set of slots. In such arrangements, the surgical instrument may further include an actuator that may be disposed adjacent to the sleeve portion, and the actuator may be configured for engaging and disengaging the positioning tip with a slot of the first and the second set of slots. In such arrangements, the actuator may be spring biased to engage the positioning tip with a slot of the first and the second set of slots.

In other arrangements, each slot of the first set of slots is aligned with a respective slot of the second set slots. The slotted portion may have a non-angled portion that defines a constant diameter and an angled portion that may extend from the non-angled portion to a larger portion that defines a diameter larger than that of the non-angled diameter. The first set of slots may be disposed radially around the non-angled portion, and the second set of slots may be disposed radially around the angled portion. The sleeve may include inner surfaces complementary to the non-angled and angled portions. The handle assembly may be pivotably attached to the sleeve by a pivot pin disposed at the pivot point.

In accordance with another aspect, a surgical instrument for inserting implants may include a body portion, a handle assembly and a sleeve portion. The body portion, defining a longitudinal axis, may have a first slot and a second slot. The handle assembly may have a handle or handgrip and a positioning tip configured to be retracted partially into the handle. The sleeve portion may be disposed around the body portion and may have an extension portion that extends away from the body portion. The handle may be pivotably attached to the sleeve portion such that the handle may pivot between a first portion and a second position. The handle (i.e., handgrip) may be orthogonal to the longitudinal axis of the body portion in the first position and may be oblique to the longitudinal axis of the body portion in the second position. The positioning tip of the handle may be disposed in the first slot in a first segment of the body portion when the handle is in the first position. The positioning tip of the handle may be disposed in the second slot in a second segment of the body portion when the handle is in the second position. In such arrangements, the body portion may include a plurality of first slots and a plurality of second slots. Both the plurality of first and second slots may be radially disposed around the body portion, and a respective longitudinal axis of each slot of the plurality of second slots may be oblique to the longitudinal axis.

The body portion may include a distal section, an intermediate section, and proximal section. The intermediate section may include the first segment and the second segment therein. The second segment may extend between the first segment and the distal section, and the distal section may have a larger diameter than that of the first segment of the intermediate section. The handle may include an elongated slot and a pivot pin that extends through the elongated slot. The handle may be threadably attached to a connector component that connects the handle and the positioning tip, and the handle may extend away from the body portion. The handle portion may include an end portion. The end portion of the handle may be disposed within the hollow interior of the extension portion. When the positioning tip is retracted from the body portion, the sleeve and the handle may rotate around the body portion while the handle is in the first position or the second position. The positioning tip may have an insertion portion having an oval shape that conforms to the first and second slots. The insertion portion may have a smaller thickness than the remainder of the positioning tip. The insertion portion of the positioning tip may be the only feature of the handle that contacts the body portion.

In accordance with yet another aspect, a surgical instrument for inserting implants may include a body portion, a handle assembly and a sleeve portion. The body portion may define a longitudinal axis. The body portion may have a slotted portion that defines a first slot and a second slot that are spaced apart from each other along the longitudinal axis of the body portion. The handle assembly may have a handle and a positioning tip that is slidably attached to the handle. The positioning tip may be partially disposed within the handle. The sleeve portion may be disposed around the slotted portion of the body portion and configured to rotate around the body portion when the positioning tip is retracted into the handle. The sleeve portion may have an extension portion that extends away from the body portion. The handle may be pivotably attached to the sleeve portion such that the handle can pivot between a first position and a second position. The handle may be orthogonal to the longitudinal axis in the first position and oblique to the longitudinal axis in the second position. The positioning tip of the handle may be disposed in the first slot in a first segment of the body portion when the handle is in the first position and may be disposed in the second slot in a second segment of the body portion when the handle is in the second position. The second segment may define a larger diameter than that of the first segment.

BRIEF DESCRIPTION OF THE DRAWINGS

A more complete appreciation of the subject matter of the present disclosure and the various advantages thereof may be realized by reference to the following detailed description which refers to the accompanying drawings, in which.

DETAILED DESCRIPTION

As used herein unless stated otherwise, the term "anterior" means toward the front part of the body, and the term "posterior" means toward the back part of the body. When referring to specific directions in the following discussion of a certain device, the terms "proximal" and "distal" are to be understood in regard to the device's orientation and position during exemplary application to human body. Thus, the term "proximal" means closer to the operator or in a direction toward the operator, and the term "distal" means more distant from the operator or in a direction away from the operator. In addition, the terms "about," "generally," and "substantially" are intended to mean that deviations from absolute are included within the scope of the term so modified.

Figure 1:
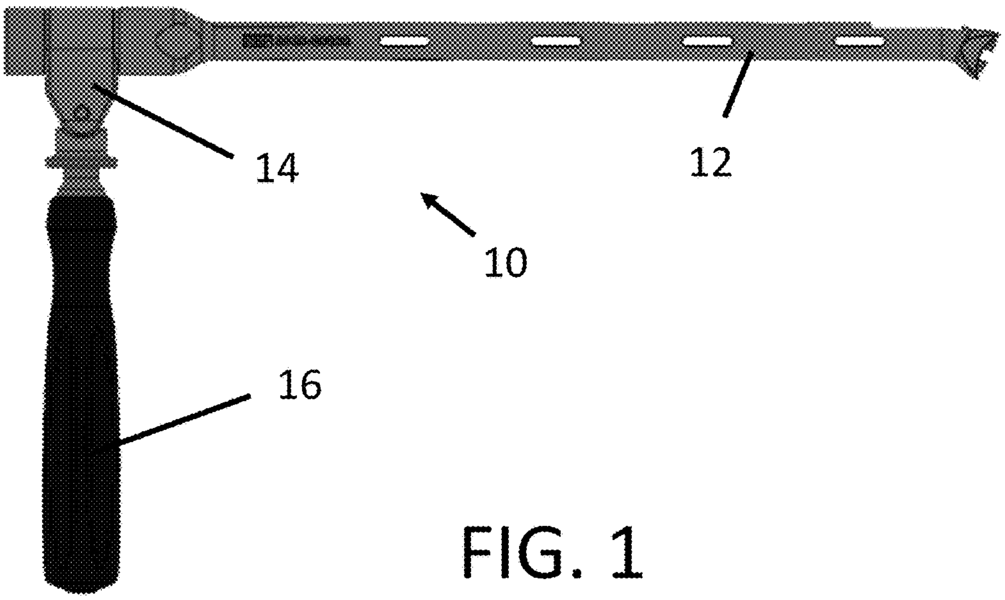
FIG. 1 is a side view of an instrument and a handle in accordance with an embodiment of the present disclosure, the handle being positioned orthogonal to the longitudinal axis of the instrument.
Figure 2:
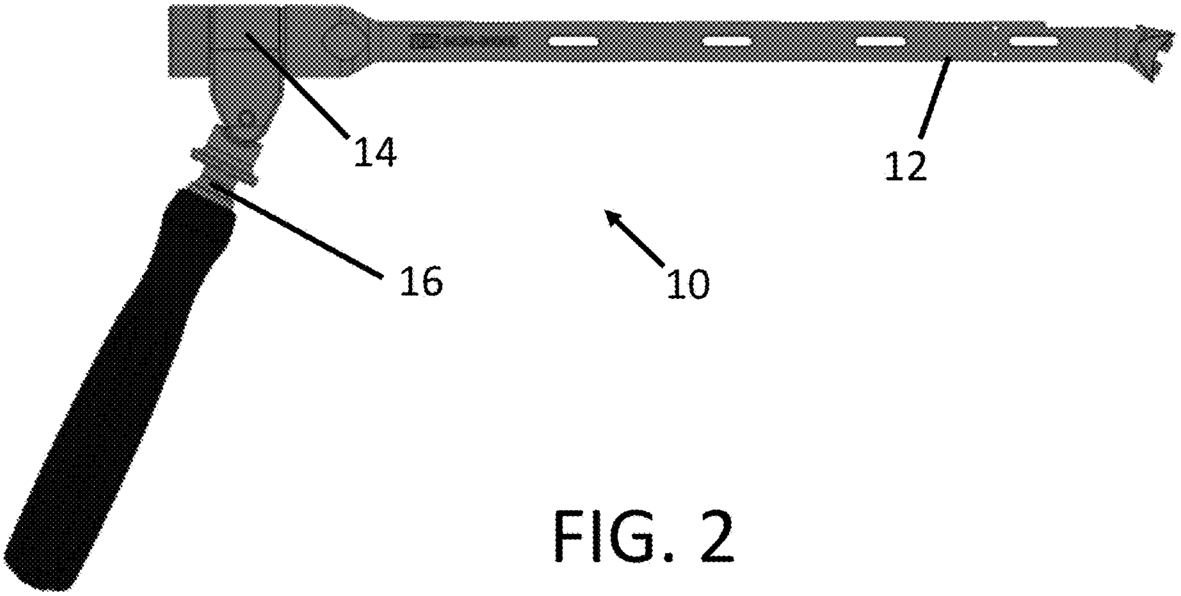
FIG. 2 is a side view of the instrument and handle of FIG. 1, the handle positioned diagonal to the longitudinal axis of the instrument.
Figure 3:
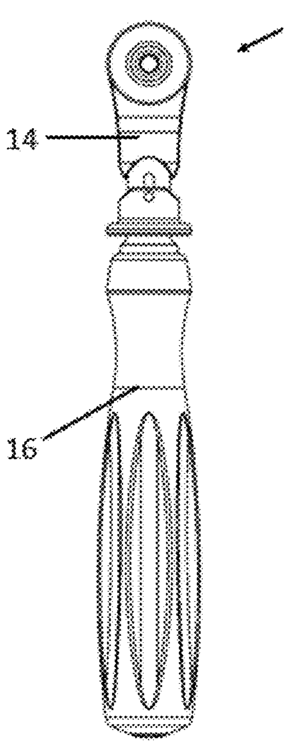
FIG. 3 is a rear view of the instrument of FIG. 1.
Figure 4:
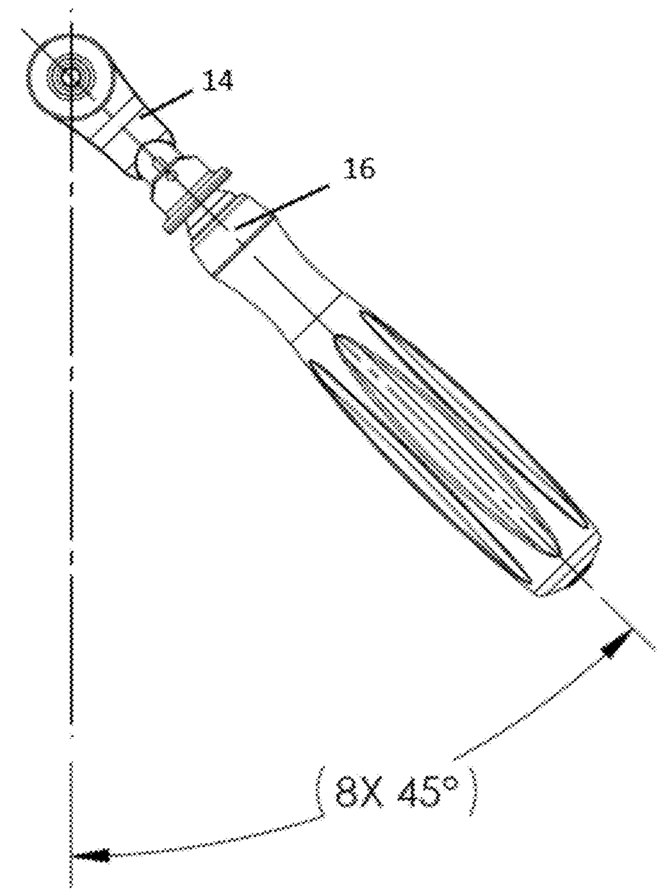
FIG. 4 is a rear view of the instrument of FIG. 3 with the handle rotated 45° counterclockwise from the position shown in FIG. 3.

In a first aspect, the present disclosure relates to a modular surgical instrument. The instrument may include a handle configured to pivot in a direction along the longitudinal axis of the shaft of the instrument, such as shown in FIGS. 1-2. Additionally, the handle of the instrument may be configured to rotate around the shaft of the instrument while the shaft remains stationary, as shown in FIGS. 3-4.

Figure 5:
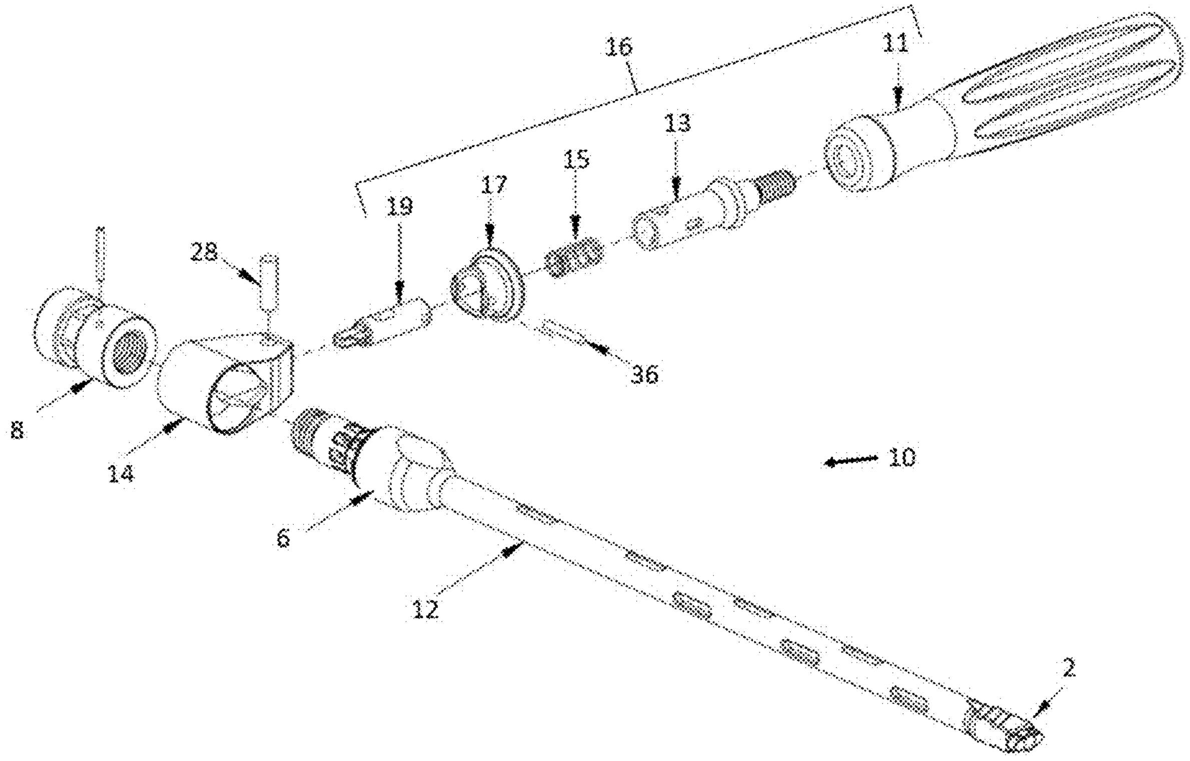
FIG. 5 is an exploded view of the instrument and handle in accordance with FIG. 1.
Figure 6:
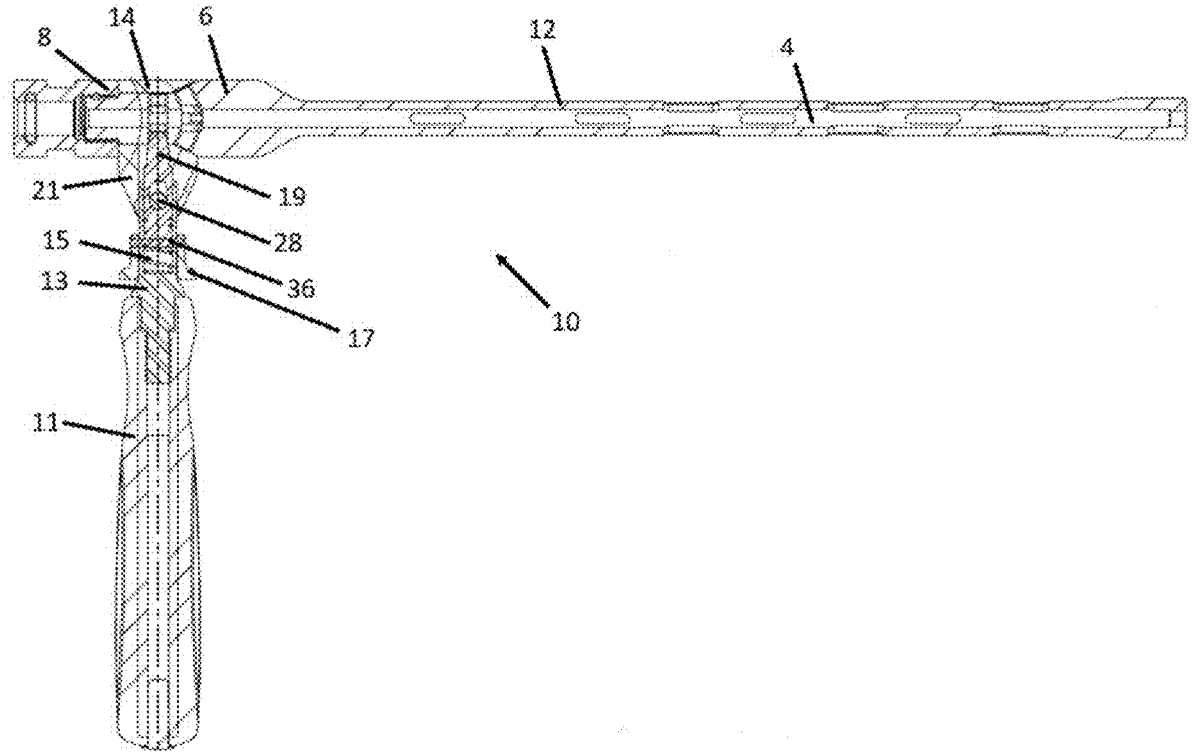
FIG. 6 is a cross sectional side view of the instrument and handle in accordance with FIG. 5.
Figure 7:
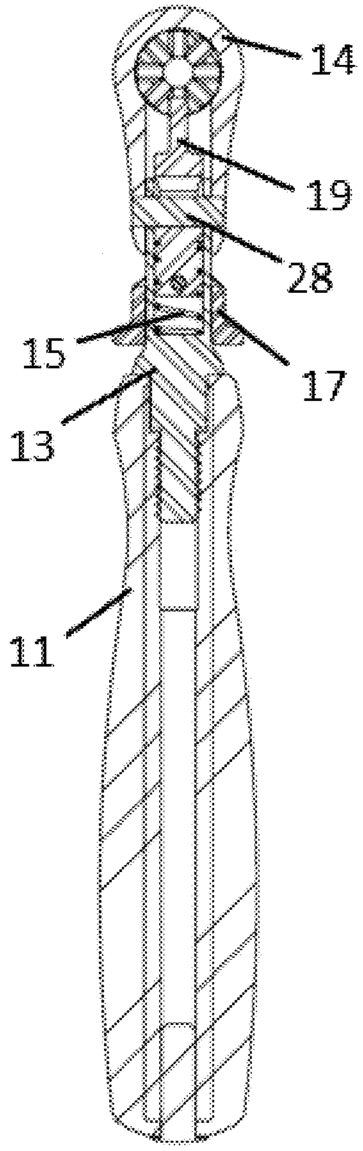
FIG. 7 is a cross-sectional rear view of the instrument of FIG. 6.

In one embodiment, instrument 10 includes a shaft 12, a sleeve 14, and a handle assembly 16 as shown in the drawings. As best shown in FIGS. 5-6, shaft 12 includes implant attachment 2, hollow annulus 4, body portion 6, and cap 8. Implant attachment 2 is located at the distal end of shaft 12 and is configured to detachably connect to an implant (e.g., a spinal fusion implant). Cap 8 is threadably connected to the proximal end of shaft 12, with body portion 6 (i.e., slotted portion) is located adjacent to cap 8.

Figure 8:
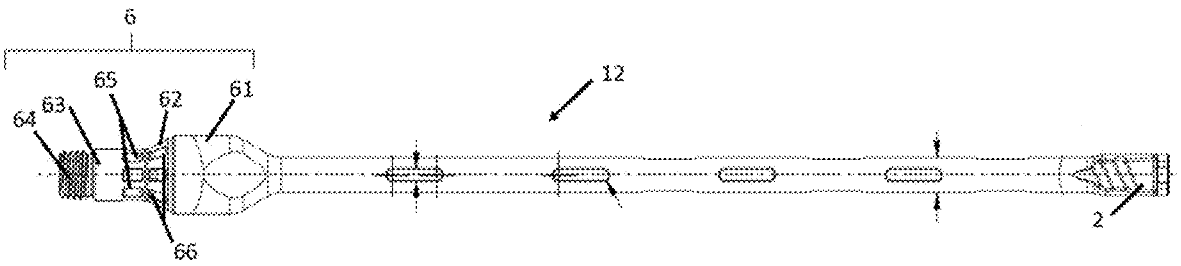
FIG. 8 is a side view of a shaft of the instrument of FIG. 5.
Figure 9:
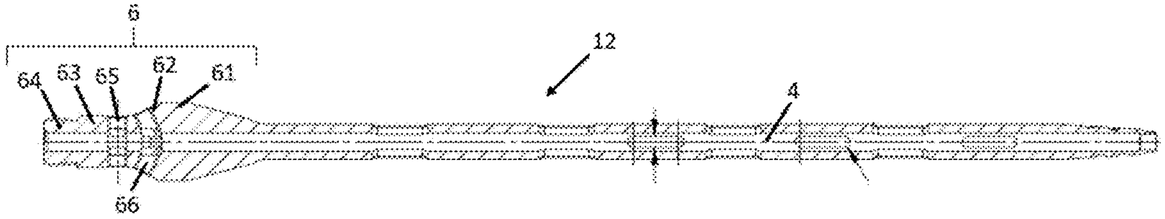
FIG. 9 is a cross sectional view of the shaft of FIG. 8.

Body portion 6 includes a distal portion 61, an intermediate section 62-63, a proximal portion 64, and a plurality of slots that are radially disposed around shaft 11, as best shown in FIGS. 8-9. Sleeve 14 is positioned between proximal portion 64 and distal portion 61 such that the sleeve covers the majority of intermediate section 62-63. Intermediate section 62-63 are divided into first segment 63 and second segment 62. First segment 63 has a smaller outer diameter than distal portion 61, and second segment 62 has an outer diameter that increases in the distal direction along the longitudinal axis defined by body portion 6, the body portion being coaxially aligned with the shaft of instrument 10. First segment 63 includes normal slots 65, and second segment 62 includes diagonal slots 66. These slots are radially disposed around the first and second segments, respectively. In some embodiments, normal slots 65 may extend into body portion 6 along a first direction that is perpendicular to the longitudinal axis defined by the body portion, and diagonal slots extend into the body portion along a second direction that is diagonal to the longitudinal axis of the body portion. First segment 63 and second segment 62 include any number of slots such that the first and second segments may have an equal or unequal number of slots. For example, first segment 63 and second segment 62 may each have eight slots that are equally dispersed around first segment 63 and second segment 62, respectively. Additionally, the location of the normal slots 65 and diagonal slots 66 may be aligned such that the normal slots and the diagonal slots are located at 45°, 90°, 135°, 180°, 225°, 270°, 315°, or 360° around body portion 6.

Sleeve 14 includes a central anulus 25 that wraps around body portion 6 and an extension portion 21 that extends away from body portion 6, as best shown in FIGS. 5-7 and 10-11. Sleeve 14 is rotatably disposed around body portion 6 adjacent to cap 8, with the cap acting to hold the sleeve longitudinally in place. Extension portion 21 includes a cavity 23 and an aperture 27. Cavity 23 extends into central anulus 25 such that the cavity and the central anulus are in communication with each other. Cavity 23 is configured to receive a portion of handle assembly 16 such that that portion of the handle assembly can slide and pivot within the sleeve (discussed in more detail below). And aperture 27 extends through both sides of the extension portion and through cavity 23.

Referring to FIGS. 5-7 and 12-16, handle assembly 16 includes a handgrip 11, a connector 13, an actuator 17, and a positioning tip 19. Handgrip 11 connects to positioning tip 19 via connector 13, and the positioning tip is partially disposed within connector 13. Handgrip 11 is threadably attached to connector 13 opposite to positioning tip 19 and adjacent to a backstop 74 on connector 13. Connector 13 has a hollow chamber 76 configured to receive positioning tip 19 and a spring 15 such that the positioning tip can slide between different locations therein. Actuator 17 is slidably disposed around hollow chamber 76 of connector 13 and connected to positioning tip 19 by an actuator pin 36 positioned within a hole 54 in actuator 17 and an elongated hole 73 of connector 13 and a bottom hole 34 of positioning tip 19 when such holes are aligned, as shown in FIG. 6. In other words, when hole 54, elongated hole 73, and bottom hole 34 are in communication with each other, actuator pin 36 is disposed therein. Spring 15 has open-coil helical springs wound to resist compression and housed within hollow chamber 76 of connector 13 between positioning tip 19 and connector 13 such that the spring may exert a force on both the positioning tip and connector 13. In this manner, spring 15 is configured to push positioning tip 19 toward body portion 6.

Figure 10:
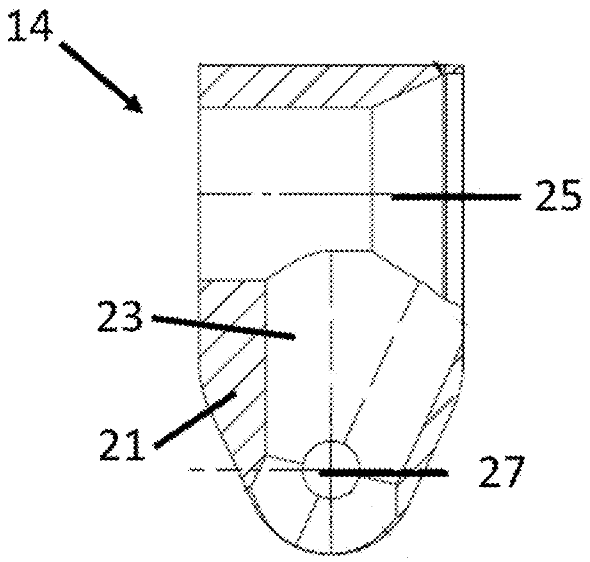
FIG. 10 is a cross sectional view of a sleeve of the instrument of FIG. 5.
Figure 11:
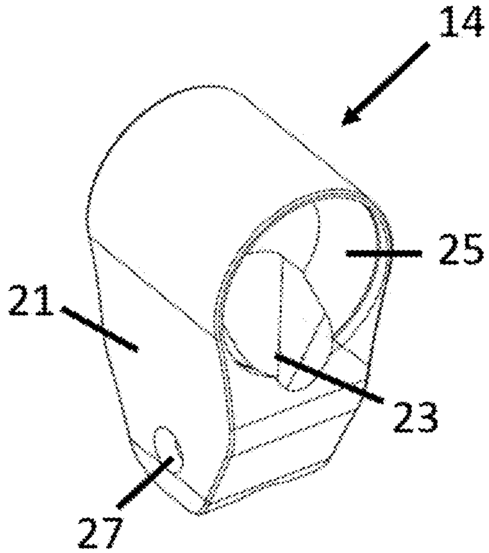
FIG. 11 is a perspective view of the sleeve of the instrument of FIG. 10.
Figure 12:
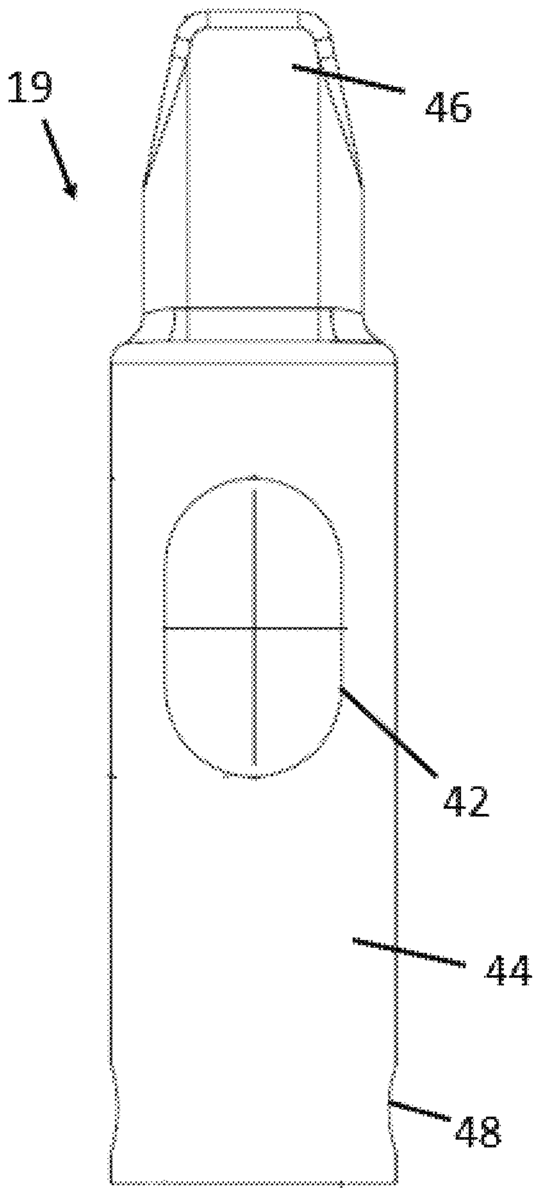
FIG. 12 is a side view of a positioning pin of the handle of FIG. 5.
Figure 13:
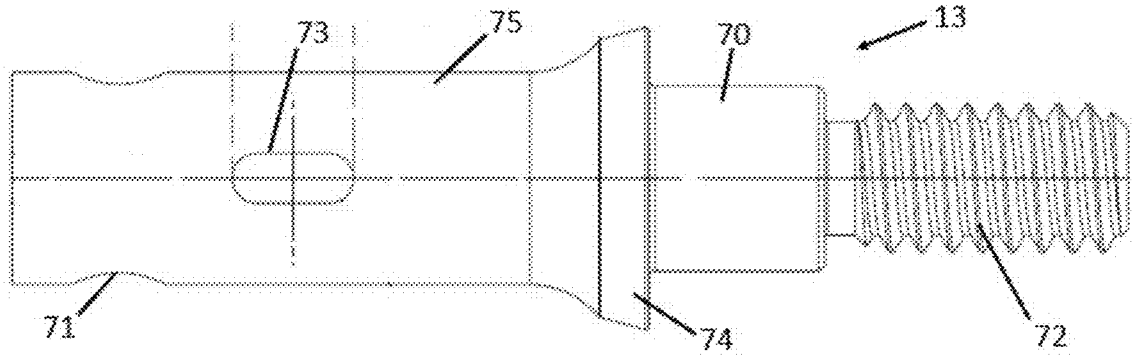
FIG. 13 is a side view of a connector of the handle of FIG. 5.
Figure 14:
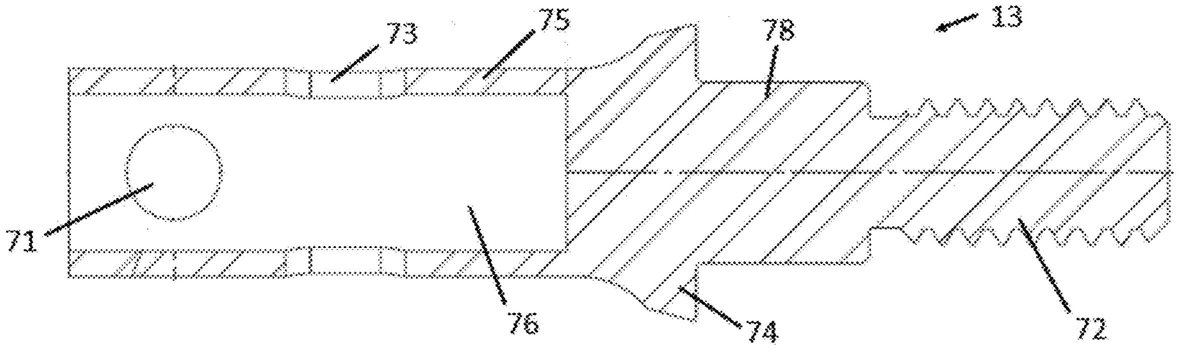
FIG. 14 is a cross sectional view of the connector of FIG. 13.
Figure 15:
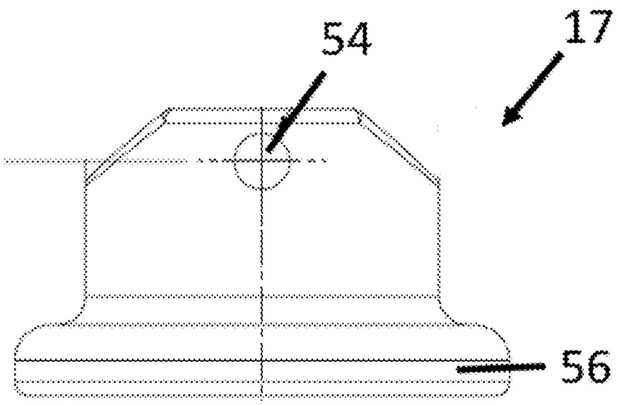
FIG. 15 is a side view of an actuator of the handle of FIG. 5.
Figure 16:
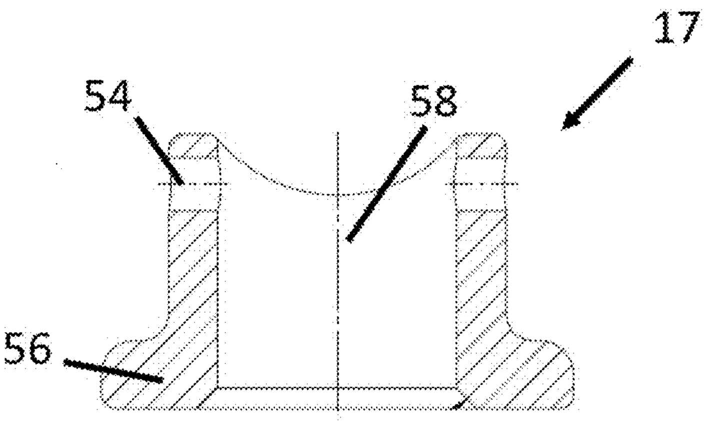
FIG. 16 is a cross-sectional side view of the actuator of FIG. 15
Figure 18:
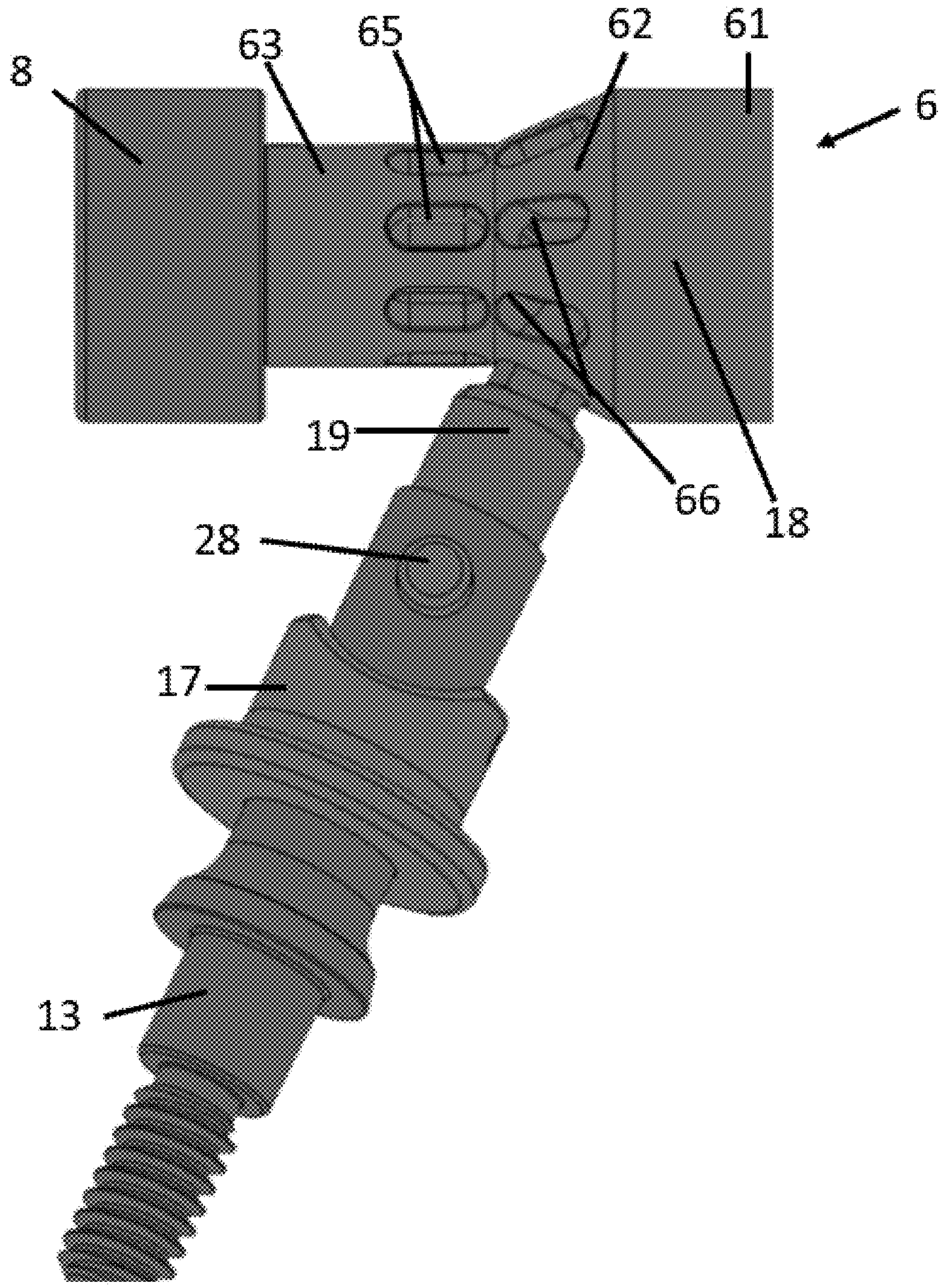
FIG. 18 is a side view of components of the handle of FIG. 2.
Figure 19:
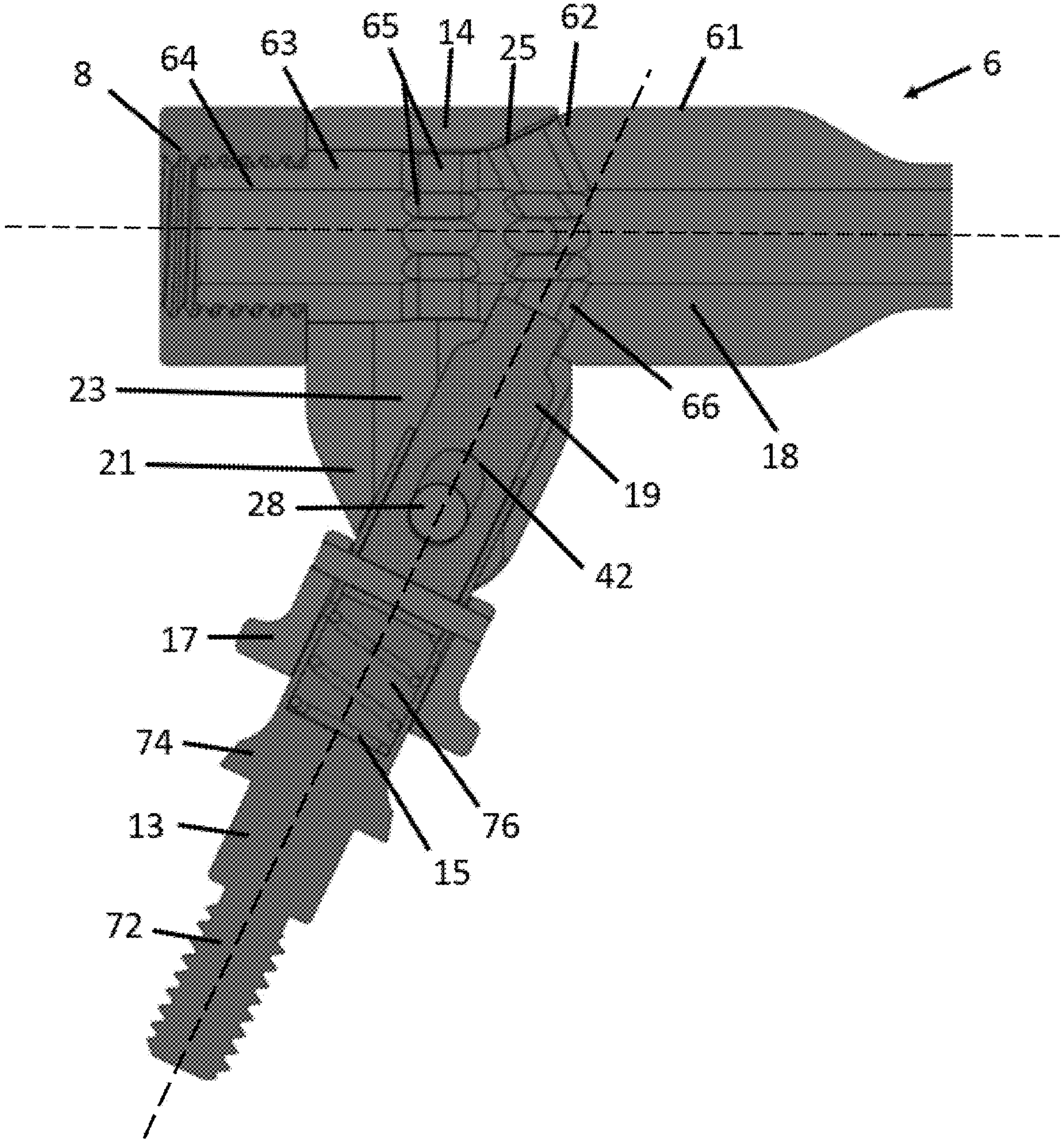
FIG. 19 is a cross sectional view of the handle of FIG. 2.

Continuing with the embodiments depicted in FIGS. 5-19, positioning tip 19 is slidably disposed within cavity 23 and pivotably connected to extension portion 21 by pivot pin 28 positioned within slot 42 of positioning tip 19 and top hole 71 of connector 13 and aperture 27 when the slot and the aperture and the slot hole are in communication with each other as shown in FIGS. 6 and 19. Cavity 23 has an hourglass-like shape with opposite ends defining wider openings than a narrow region therebetween. In some embodiments, aperture 27 may be located at this narrow region of cavity 23, as shown in FIG. 10. Under such an arrangement, positioning tip 19 is provided space to pivot within cavity 23 about pivot pin 28, which defines the pivot point of handgrip 11.

Figure 17:
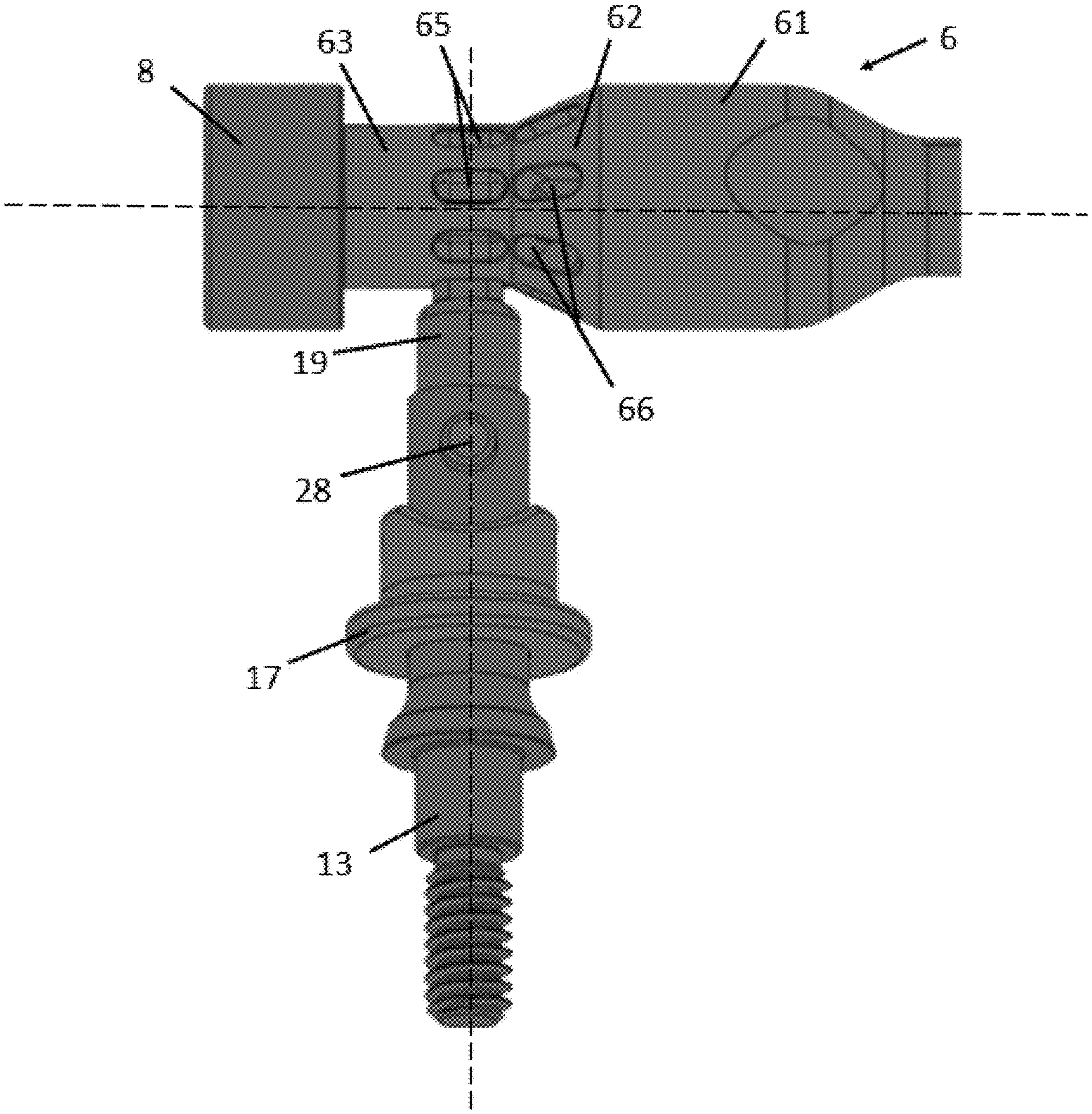
FIG. 17 is a side view of components of the handle of FIG. 1.

As best shown in FIGS. 17-19, Normal slots 65 and diagonal slots 66 are configured to receive a portion of positioning tip 19. For example, positioning tip 19 has first end 46 that has a smaller width and thickness than the remainder of the positioning tip such that the pointed end can be positioned within either a normal slot 65 or diagonal slot 66.

Continuing with FIG. 19, anulus 25 of sleeve 14 has a cross sectional profile that mirrors a cross-sectional profile of intermediate section 62-63 such that any change in the outer diameter of the intermediate section corresponds to a change in the inner diameter of the annulus. Cavity 23 of sleeve 14 is in communication with at least one normal slot 65 and one diagonal slot 66 at various positions around body portion 6. In this manner, sleeve 14 may be configured to align positioning tip 19 with normal slots 65 and/or diagonal slots 66 for insertion therein.

Figure 20:
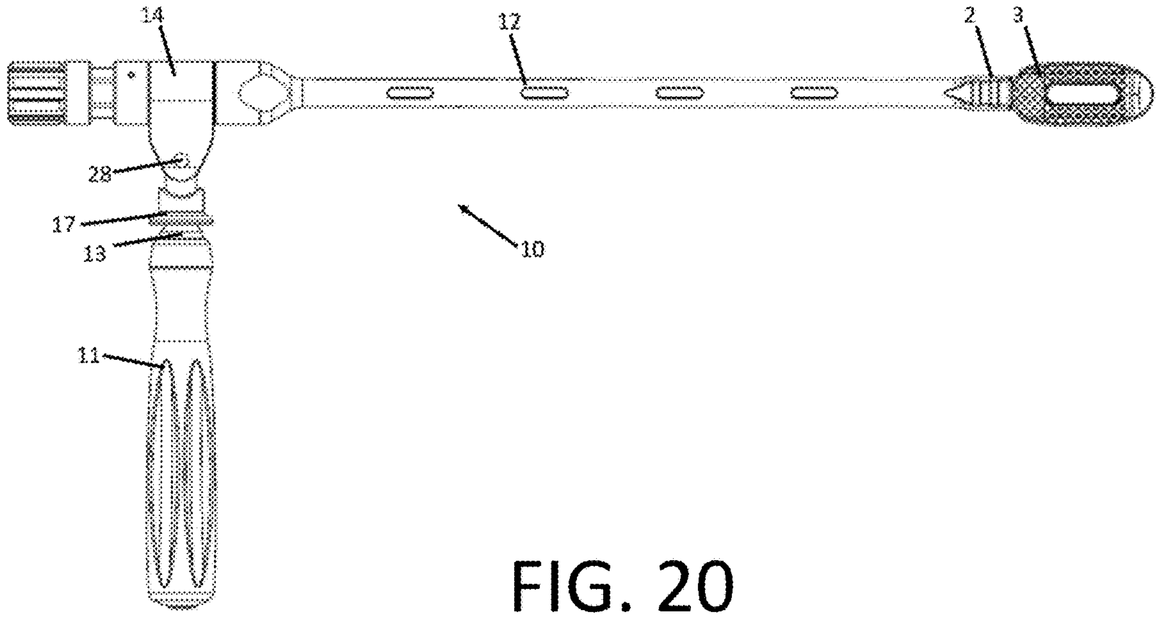
FIG. 20 is a side view of the instrument of FIG. 5, the instrument arranged to insert a spinal implant via a direct approach.
Figure 21:
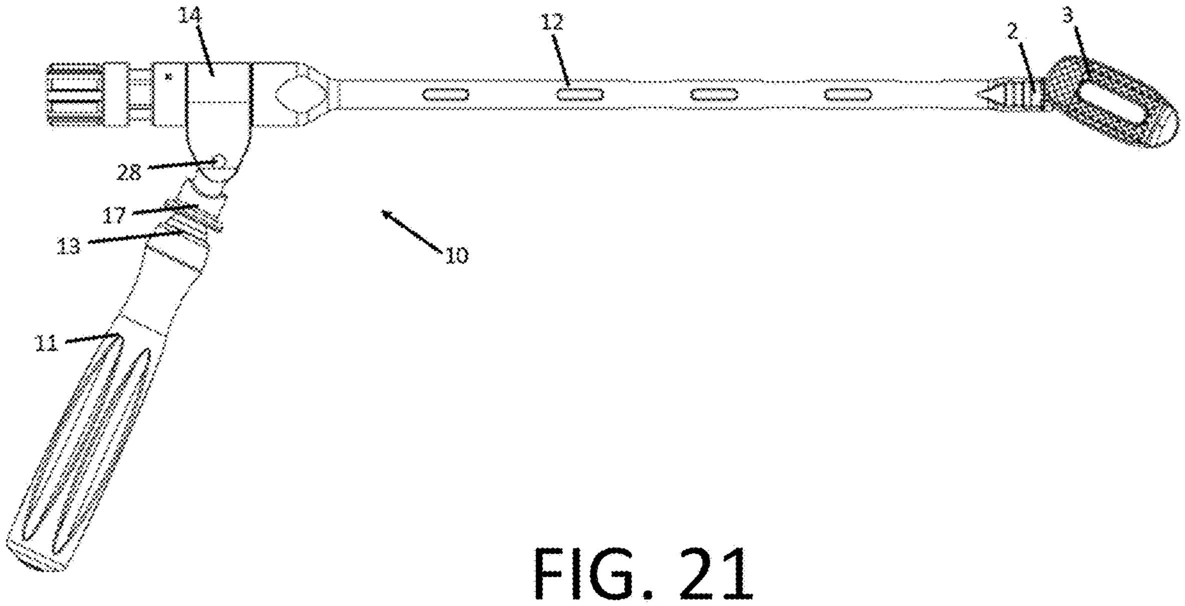
FIG. 21 is a side view of the instrument of FIG. 20, the instrument arranged to insert a spinal implant via an angled approach.

As shown in FIGS. 20-21, attachment tip 2 is configured to change the orientation of the implant attached thereon between a non-angled position to an angled position with respect to the longitudinal axis of the shaft of the instrument and/or the body portion of the handle assembly. Attachment tip may also be a modular attachment mechanism configured to attach to various implants of different shapes, sizes, and structure. In some embodiments, an attachment mechanism located at the tip of instrument 10 may be capable of pivoting between two or more positions. In such instances, an attached implant may be tilted as the attachment mechanism pivots to and angled position with respect to the longitudinal axis of the shaft of the instrument. The attachment mechanism may releasably attach to an implant via components that hook or clamp together. Alternatively, in some embodiments, an inner shaft may extend from attachment tip 2 and threadably connect to an implant.

In another aspect, the present invention relates to a kit that may include a surgical instrument having a rotatable and pivotable handle, such as handgrip 11, along with implants, for example, but no limited to, spinal implants of various shapes and sizes. The kit may also include additional surgical tools such as retractors and cutting tools that may be used in a surgical procedure.

In yet another aspect, the present disclosure relates to a method of pivoting a handle of a surgical instrument along the longitudinal axis of the shaft of the instrument. For example, handgrip 11 may pivot from a first position to a second position by retracting positioning tip 19 away from a normal slot 65 such that spring 15 is compressed within hollow chamber 76 of connector 13 by pulling actuator 17 toward backstop 74 and holding the actuator in this retracted position. Once the positioning tip 19 is fully disengaged from body portion 6, connector 13 may be tilted by pulling handgrip 11 proximally such that first end 46 of positioning tip 19 pivots about pivot pin 28 toward the distal tip of instrument 10 within cavity 23 of sleeve 14 as the handgrip pivots away from the distal tip of the instrument. In other words, pulling handgrip 11 in a proximal direction causes positioning tip 19, connector 13, and handgrip to pivot about pivot pin 28 such that the central axis of the connector becomes diagonal (i.e., oblique) to the longitudinal axis of body portion 6, as shown in FIG. 19. Once first end 46 of positioning tip 19 has pivoted forward within cavity 23, the diagonal position of handgrip 11 may be secured by releasing actuator 17 such that spring 15 pushes first end 46 of positioning tip 19 into a diagonal slot 66 that is aligned with cavity 23 of sleeve 14. Handgrip 11 may pivot back to the previous orientation by repeating the foregoing steps but instead pushing handgrip 11 toward the distal tip of instrument 10 such that the central axis of the handgrip and connector 70 become orthogonal to the longitudinal axis of body portion 6 and/or the shaft of the instrument, as shown in FIG. 17. In this manner, handgrip 11 may be pivoted from an orthogonal position to a diagonal position and back when in a disengaged state. This provides the advantage of allowing medical personnel to change the angle in which a handle, such as handgrip 11, extends from a surgical instrument to best suit a surgical procedure. In other embodiments, handgrip 11 may also pivot from the orthogonal position to another oblique position, i.e., a third position (not shown), where connector 13 is tilted by pushing the handgrip distally such that first end 46 of positioning tip 19 pivots about pivot pin 28 away from the distal tip of instrument 10 within cavity 23 of sleeve 14 as the handgrip pivots toward the distal tip of the instrument. In such instances, body portion 6 of instrument 10 may include a third set of diagonal slots (not shown) disposed proximal to normal slots 65 and configured to receive first end 46 to allow handgrip 11 to be fixed in the third position. Additionally, an implant attached to instrument 10, such as implant 3, may be positioned such that the longitudinal axis of the implant is oblique to the longitudinal axis of body portion 6. In this manner, medical personnel can adjust the orientation of the implant and handgrip in a way that best facilitates implantation of the implant.

In another aspect, the present disclosure relates to a method of rotating a handle of a surgical instrument around the longitudinal axis of the shaft of the instrument. For example, handgrip 11 may rotate from a first location to a second location by retracting positioning tip 19 away from body portion 6 such that spring 15 is compressed within hollow chamber 76 of connector 13 by pulling actuator 17 toward backstop 74 and holding the actuator in this retracted position. Once the positioning tip 19 is fully disengaged from body portion 6, handgrip 11 may be rotated by moving handgrip 11 around body portion 6, as shown in FIGS. 3-4. In some embodiments, handgrip 11 may be rotated and secured to different locations around body portion 6. For example, angle slots 66 and non-angled slots 65 may be disposed at eight different locations around body portion 6 and spaced apart by 45°, but other embodiments may have more or less locations. Once positioning tip 19 is aligned with a different slot disposed around body portion 6, the second location of handgrip 11 may be secured by releasing actuator 17 such that spring 15 pushes first end 46 of positioning tip 19 into either a normal slot 65 or a diagonal slot 66 aligned with cavity 23 of sleeve 14. Handgrip 11 may be rotated back a previous location or further rotated around body portion 6 by repeating the foregoing steps and rotating handgrip 11 such that the positioning tip 19 aligns with a slot at a different location around body portion 6, as shown in FIGS. 17-19. In this manner, handgrip 11 may be relocated by rotating the handle around body portion 6 to various locations. This provides the advantage of allowing medical personnel to change the location in which a handle, such as handgrip 11, extends from a surgical instrument to best suit a surgical procedure.

In another aspect, the present disclosure relates to a method of rotating and pivoting a handle of a surgical instrument around and along the longitudinal axis of the shaft instrument. For example, handgrip 11 may rotate from a first location to a second location and pivot from a first position to a second position by retracting positioning tip 19 away from body portion 6 such that spring 15 is compressed within hollow chamber 76 of connector 13 by pulling actuator toward backstop 74 and holding the actuator in this retracted position. Once the positioning tip 19 is fully disengaged from body portion 6, handgrip 11 may be rotated around and pivoted along body portion 6 by moving handgrip 11 around and along the longitudinal axis of the body portion and/or the shaft of instrument 10, as shown in FIGS. 3-4 and 1-2, respectively. Once positioning tip 19 is aligned with a different slot disposed around body portion 6, a new orientation of handgrip 11 may be secured by releasing actuator 17 such that spring 15 pushes pointed end 46 of positioning tip 19 into a slot 65, 66 disposed in body portion 6. Handgrip 11 may be reoriented back to the previous position or further reorientated about body portion 6 by repeating the foregoing steps. In this manner, handgrip 11 may be oriented by rotating and pivoting the handle around body portion 6 to various positions and angles. This provides the advantage of allowing medical personnel to select an orientation of handgrip 11 that best suits the surgical procedure.

In another aspect, the present disclosure relates to a method of pivoting a handle of a surgical instrument along the longitudinal axis of the shaft instrument and titling the orientation of an implant attached to the tip of the instrument. For example, handgrip 11 may reorient to a diagonal position by disengaging positioning pin 19 and pivoting the handgrip as described above. Before or after handgrip 11 has been pivoted to the diagonal position and positioning tip 19 has inserted into body portion 6, implant 3 may be connected to instrument 10 by attaching implant to the tip of the instrument via an attachment mechanism. Once implant 3 has been attached to instrument 10, implant 3 may be reoriented by tilting the implant such that the longitudinal axis of the implant is diagonal to the longitudinal axis of the shaft of the instrument, as shown in FIG. 21. Alternatively, the instrument may engage or attach to an implant at different locations on the implant such that the implant may be oriented in a non-angled or angled position relative to the instrument. In this manner, handgrip 10 and implant 3 can be oriented to better suit an angled approach.

It is to be understood that the disclosure set forth herein includes any possible combinations of the particular features set forth above, whether specifically disclosed herein or not. For example, where a particular feature is disclosed in the context of a particular aspect, arrangement, configuration, or arrangement, that feature may also be used, to the extent possible, in combination with and/or in the context of other particular aspects, arrangements, configurations, and arrangements of the technology, and in the technology generally.

Furthermore, although the technology herein has been described with reference to particular features, it is to be understood that these features are merely illustrative of the principles and applications of the present technology. It is therefore to be understood that numerous modifications, including changes in the sizes of the various features described herein, may be made to the illustrative arrangements and that other arrangements may be devised without departing from the spirit and scope of the present technology. In this regard, the present technology encompasses numerous additional features in addition to those specific features set forth in the claims below. Moreover, the foregoing disclosure should be taken by way of illustration rather than by way of limitation as the present technology is defined by the claims set forth below.

The invention claimed is:

1. A surgical instrument to implant spinal implants, comprising:

a shaft defining a longitudinal axis and having a slotted portion that defines a first set of slots and a second set of slots;

a sleeve rotatably disposed around the slotted portion; and a handle assembly pivotably attached to the sleeve, the handle assembly having a positioning tip sized to be received by each slot of the first and the second set of slots, wherein the handle assembly can pivot about a pivot point between a first position and a second position, wherein in the first position, the positioning tip is oriented to engage a slot of the first set of slots, and wherein in the second position, the positioning tip is oriented to engage a slot of the second set of slots.

2. The surgical instrument of claim 1, further comprising an actuator disposed adjacent to the sleeve, the actuator adapted for engaging and disengaging the positioning tip with a slot of the first and the second set of slots.

3. The surgical instrument of claim 2, wherein the positioning tip is spring biased to engage with a slot of the first and the second set of slots.

4. The surgical instrument of claim 1, wherein each slot of the first set of slots are aligned with a respective slot of the second set of slots.

5. The surgical instrument of claim 1, wherein the slotted portion includes a non-angled portion that has a constant diameter and an angled portion that extends from the non-angled portion to a larger portion that defines a diameter larger than that of the non-angled diameter, wherein the first set of slots is disposed radially around the non-angled portion, and the second set of slots is disposed radially around the angled portion.

6. The surgical instrument of claim 5, wherein the sleeve includes a plurality of inner surfaces complementary to the non-angled and angled portions.

7. The surgical instrument of claim 1, wherein the handle assembly is pivotably attached to the sleeve by a pivot pin that is disposed at the pivot point.

8. A surgical instrument for inserting implants, comprising:

a body portion defining a longitudinal axis, the body portion having a first slot and a second slot;

a handle assembly having a handle and a positioning tip that is configured to be retracted partially into the handle; and a sleeve portion disposed around the body portion, the sleeve portion having an extension portion that extends away from the body portion, wherein the handle is pivotably attached to the sleeve portion such that the handle can pivot between a first position and a second position, the handle being orthogonal to the longitudinal axis in the first position and oblique to the longitudinal axis in the second position, and wherein the positioning tip of the handle is disposed in the first slot in a first segment of the body portion when the handle is in the first position and disposed in the second slot in a second segment of the body portion when the handle is in the second position.

9. The surgical instrument of claim 8, wherein the body portion includes a plurality of first slots and a plurality of second slots both radially disposed around the body portion, and wherein a respective longitudinal axis of each slot of the plurality of second slots is oblique to the longitudinal axis of the body portion.

10. The surgical instrument of claim 8, wherein the body portion includes a distal section, an intermediate section, and proximal section, the intermediate section having the first segment and second segment therein, the second segment extending between the first segment and the distal section, and the distal section having a larger diameter than that of the first segment of the intermediate section.

11. The surgical instrument of claim 10, wherein the sleeve portion is rotatably disposed around the intermediate section of the body portion.

12. The surgical instrument of claim 8, wherein the handle includes an elongated slot and a pivot pin that extends through the elongated slot.

13. The surgical instrument of claim 8, wherein the handle is threadably attached to a connector component that connects the handle and the positioning tip, the handle extending away from the body portion.

14. The surgical instrument of claim 13, wherein the extension portion of the sleeve portion defines a hollow interior, wherein an end portion of the handle is disposed within the hollow interior of the extension portion.

15. The surgical instrument of claim 14, wherein the hollow interior of the extension portion has an hourglass-like shape to allow the end portion of the handle to pivot between the first and second positions when the positioning tip is retracted from the body portion.

16. The surgical instrument of claim 8, wherein, when the positioning tip is retracted from the body portion, the sleeve portion and the handle can rotate around the body portion while the handle is in the first position or the second position.

17. The surgical instrument of claim 14, wherein the end portion of the handle includes the positioning tip and the connector component, the connector component having a hollow chamber configured to receive a spring and at least a portion of the positioning tip, the spring disposed between the positioning tip and the connector component within the hollow chamber.

18. The surgical instrument of claim 17, wherein the handle includes a collar slidably disposed around the hollow chamber and configured for engaging and disengaging the positioning tip with either one of the first or the second slots.

19. The surgical instrument of claim 9, wherein the positioning tip has an insertion portion having an oval shape that conforms to the first and second slots, the insertion portion having a smaller thickness than the remainder of the positioning tip, and wherein the insertion portion of the positioning tip is the only feature of the handle that contacts the body portion.

20. A surgical instrument for inserting implants, comprising:

a body portion defining a longitudinal axis, the body portion having slotted portion that defines a first slot and a second slot that are spaced apart from each other along the longitudinal axis of the body portion;

a handle assembly having a handle and a positioning tip that is slidably attached to the handle, the positioning tip is partially disposed within the handle; and a sleeve portion disposed around the slotted portion of the body portion and configured to rotate around the body portion when the positioning tip is retracted into the handle, the sleeve portion having an extension portion that extends away from the body portion, wherein the handle is pivotably attached to the sleeve portion such that the handle can pivot between a first position and a second position, the handle being orthogonal to the longitudinal axis in the first position and oblique to the longitudinal axis in the second position, and wherein the positioning tip of the handle is disposed in the first slot in a first segment of the body portion when the handle is in the first position and disposed in the second slot in a second segment of the body portion when the handle is in the second position, the second segment defining a larger diameter than that of the first segment.

* * * * *